(12) United States Patent
Sagalés Mañas et al.

(10) Patent No.: US 10,188,815 B2
(45) Date of Patent: Jan. 29, 2019

(54) LARYNGEAL MASK WITH RETRACTABLE RIGID TAB AND MEANS FOR VENTILATION AND INTUBATION

(71) Applicant: Medcom Flow S.A., Barcelona (ES)

(72) Inventors: Juan Sagalés Mañas, Barcelona (ES); Alejandro Roca De Viñals Delgado, Barcelona (ES); Alberto Calaf Alcalde, Barcelona (ES)

(73) Assignee: Medcom Flow S.A., Barcelona (ES)

(*) Notice: Subject to any disclaimer, the term of this patent is extended or adjusted under 35 U.S.C. 154(b) by 602 days.

(21) Appl. No.: 14/772,850

(22) PCT Filed: Mar. 6, 2013

(86) PCT No.: PCT/ES2013/070138
§ 371 (c)(1),
(2) Date: Sep. 4, 2015

(87) PCT Pub. No.: WO2014/135715
PCT Pub. Date: Sep. 12, 2014

(65) Prior Publication Data
US 2016/0008562 A1   Jan. 14, 2016

(51) Int. Cl.
*A61M 16/04* (2006.01)
*A61B 1/267* (2006.01)
*A61B 1/00* (2006.01)

(52) U.S. Cl.
CPC ..... *A61M 16/0447* (2014.02); *A61B 1/00052* (2013.01); *A61B 1/267* (2013.01); *A61M 16/04* (2013.01); *A61M 16/0409* (2014.02); *A61M 16/0415* (2014.02); *A61M 16/0488* (2013.01); *A61M 2202/0208* (2013.01); *A61M 2205/8206* (2013.01)

(58) Field of Classification Search
CPC .......... A61M 1/267; A61M 16/0434–16/0459; A61M 16/0465–16/0497; A61M 16/0409
USPC ........................................................ 600/188
See application file for complete search history.

(56) References Cited

U.S. PATENT DOCUMENTS

| | | | |
|---|---|---|---|
| 5,287,484 A * | 2/1994 | Nishii | ................. G06F 12/0897 711/120 |
| 5,303,697 A | 4/1994 | Brain | |
| 5,623,921 A | 4/1997 | Kinsinger et al. | |
| 5,665,052 A * | 9/1997 | Bullard | ................ A61B 1/2676 600/194 |
| 5,682,880 A | 11/1997 | Brain | |

(Continued)

FOREIGN PATENT DOCUMENTS

| | | |
|---|---|---|
| EP | 1 938 855 A1 | 7/2008 |
| GB | 2 234 040 A | 10/1998 |

(Continued)

*Primary Examiner* — Nyca T Nguyen
(74) *Attorney, Agent, or Firm* — Ladas & Parry LLP

(57) ABSTRACT

A laryngeal mask including a rigid hollow tube essentially in the form of a "J", and which has a lengthwise opening along its entire length, and a flexible tube, also essentially in the form of a "J", configured to be housed in the lengthwise opening of the rigid hollow tube, and which can be separated from it. This provides a configuration for a laryngeal mask that can change from having rigid properties to flexible ones at the doctor's will, without the need to interrupt the patient's supply of oxygen at any time.

21 Claims, 16 Drawing Sheets

(56) References Cited

U.S. PATENT DOCUMENTS

Figure 1:
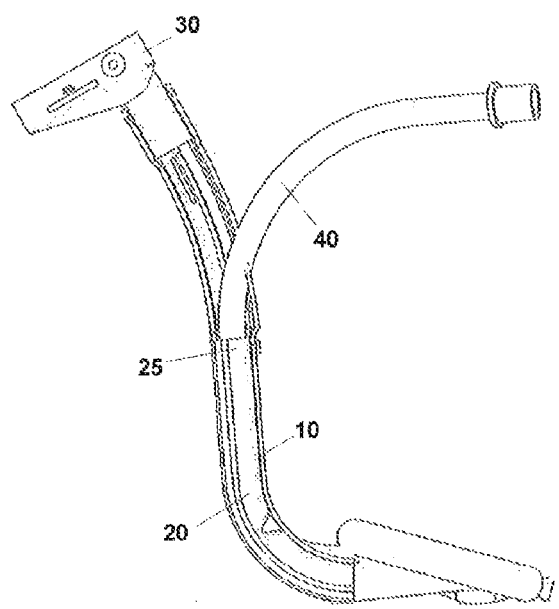

| | | | |
|---|---|---|---|
| 6,070,581 A * | 6/2000 | Augustine | A61B 1/267 128/200.26 |
| 7,128,071 B2 * | 10/2006 | Brain | A61M 16/04 128/207.15 |
| 7,546,838 B2 * | 6/2009 | Lin | A61M 16/04 128/207.14 |
| 7,946,981 B1 | 5/2011 | Cubb | |
| 8,220,461 B1 * | 7/2012 | Guerra | A61M 16/0463 128/200.26 |
| 2001/0012923 A1 | 8/2001 | Christopher | |
| 2001/0014768 A1 * | 8/2001 | Kaplan | A61B 1/07 600/188 |
| 2002/0189618 A1 | 12/2002 | Augustine et al. | |
| 2003/0037790 A1 * | 2/2003 | Brain | A61M 16/04 128/207.14 |
| 2003/0192548 A1 | 10/2003 | Chang | |
| 2004/0020491 A1 | 2/2004 | Fortuna | |
| 2004/0079364 A1 | 4/2004 | Christopher | |
| 2007/0106117 A1 * | 5/2007 | Yokota | A61B 1/042 600/120 |
| 2007/0240722 A1 | 10/2007 | Kessler | |
| 2009/0125002 A1 * | 5/2009 | Totz | A61M 16/04 604/528 |
| 2009/0194102 A1 * | 8/2009 | Chen | A61M 16/0488 128/202.13 |
| 2011/0196203 A1 | 8/2011 | Xiao et al. | |
| 2012/0174929 A1 * | 7/2012 | Esnouf | A61M 16/04 128/207.15 |
| 2013/0066151 A1 * | 3/2013 | Chen | A61B 1/267 600/188 |
| 2015/0165148 A1 * | 6/2015 | Kozlowski | A61M 16/0434 128/200.26 |

FOREIGN PATENT DOCUMENTS

| | | |
|---|---|---|
| MX | PA05000952 A | 9/2005 |
| WO | 2004/073510 A1 | 9/2004 |
| WO | 2007/085664 A1 | 8/2007 |
| WO | 2011/060447 A1 | 5/2011 |

* cited by examiner

LARYNGEAL MASK WITH RETRACTABLE RIGID TAB AND MEANS FOR VENTILATION AND INTUBATION

CROSS-REFERENCE TO RELATED APPLICATION

This U.S. application claims priority under 35 U.S.C 371 to, and is a U.S. National Phase application of, the International Patent Application No. PCT/ES2013/070138, flied 6 Mar. 2013, the disclosures of which are incorporated in their entirety by reference herein.

TECHNICAL FIELD

The present invention is within the field of anaesthesia for both the initial anaesthesia phase and the intermediate or late anaesthesia phase and in both the ventilation mode and intubation mode for administering oxygen to the patient.

The purpose of the invention is focused on a laryngeal video mask that allows such interventions to take place under much more advantageous conditions than those currently existing in the state of the art since its properties can be changed from rigid to flexible at any time according to the needs related to administration of the anaesthesia. For example, if the anaesthesia is in its initial moments a rigid system is required, while after the anaesthesia has passed beyond those initial moments and is in its intermediate or final moments of the surgical intervention, a soft and flexible system is then required. The laryngeal video mask proposed also allows such interventions to take place under much more advantageous conditions compared to those that currently exist in the state of the art, by allowing oxygenation of the patient in both the ventilation and/or intubation mode according to the clinical needs of the patient. Throughout its entire process of use, whether in rigid or flexible mode as well as in ventilation mode or intubation mode, a continuous view of the airway can be maintained at all times during the anaesthesia, thanks to its optical systems. These comprise an optical lens integrated into the laryngeal video mask, an optical lens integrated into the distal portion of the viewing system, a video camera viewing system, an illumination system, and an integrated anti-condensation system.

STATE OF THE ART

Administration of oxygen to the patient is one of the anaesthetist's priorities when providing anaesthesia to the patient during surgery. The anaesthetist can administer oxygen to the patient once the patient is unconscious in ventilation mode or if can be administered to the unconscious patient in intubation mode. If the patient does not have a pre-existing illness and if the surgery is not complicated and is of short duration, the ventilation devices typically used to administer oxygen to the patient are those such as laryngeal masks with a distal inflatable or gel ring. However, if the patient has many pre-existing illnesses, if the surgery is complicated and involves vital organs, if it is of long duration, or if the patient will later be transferred to the hospital's Intensive Care Unit, intubation devices such as laryngoscopes are typically used to introduce an endotracheal tube into the trachea in order to administer oxygen to the patient.

However, if based upon the patient's clinical condition the doctor chooses to begin to administer the anaesthesia with one means of ventilation or intubation but then for various reasons the situation becomes complicated and the manoeuvre cannot be correctly performed and if oxygen therefore cannot be administered to the patient, the doctor will have a very serious problem. The patient could die if the oxygenation is not restored in about five minutes.

For example, if the doctor has chosen a means of intubation such as with a laryngoscope but the intubation procedure is not performed correctly and the administration of oxygen to the patient fails, the oxygenation must be restored using a means of ventilation such as a laryngeal mask with an inflatable ring or gel ring. The first means (the laryngoscope) must be removed and then the means of ventilation such as the laryngeal mask with inflatable ring or gel ring must immediately be introduced. Many minutes are lost in this manoeuvre and it is very risky for the patient since if is necessary to first remove the initial intubation device, then to look for a recovery device such as a laryngeal mask, then to introduce this recovery device correctly into the patient's larynx, and finally to ventilate and administer oxygen, etc. All of this can cause the greater part of those approximately five minutes to be lost and during this time the patient's brain may be without oxygen and death can later result.

Conversely, if the doctor has chosen a means of ventilation such as a laryngeal mask with inflatable ring or gel ring for intubation but the ventilation procedure cannot be performed correctly and the administration of oxygen to the patient fails, oxygenation must be restored with a means of intubation such as a laryngoscope, by removing the laryngeal mask and immediately introducing the laryngoscope. Several minutes are also lost in this manoeuvre and it is very risky for the patient since it is necessary to first remove the initial ventilation device, then to look for a recovery intubation device such as a laryngoscope, then to introduce this recovery device correctly into the patient's larynx, then to intube with an endotracheal tube and administer oxygen, etc. All of this can cause the greater part of those approximately five minutes to be lost, and during this time the patient's brain may be without oxygen and death can later result.

Also, the devices that currently exist in the state of the art either have rigid physical properties or soft and flexible physical properties. Devices such as laryngoscopes typically have rigid properties and they are therefore good for the initial phase of anaesthesia; in other words, for the initial moments. Because of their rigidity they can be easily introduced and placed in their correct position in the airway and they also allow the tissues of the airway to be separated towards the sides. In this way the endotracheal tube can be introduced from the exterior of the mouth towards the interior of the airway and then past the vocal cords towards the trachea. The primary inconvenience of these rigid laryngoscopes is that they cannot be kept inside the patient's airway for a long time, since their rigid properties put pressure on soft areas of the airway tissues causing injuries and sores. For this reason, a few minutes after intubation these laryngoscopes must be removed, leaving in their place a soft or flexible endotracheal tube made of PVC or silicone in order to administer oxygen to the patient.

On the other hand, laryngeal mask type devices with an inflatable ring or gel ring have soft and flexible properties and they are therefore good for use during the administration of anaesthesia after the initial phase; in other words, for the intermediate or final phases of the anaesthesia, because their soft and flexible properties allow them to be kept inside of the patient's airway for a much longer period of time in contact with the airway's soft tissues where they do not produce pressure, injuries, or sores during administration of oxygen to the patient.

However, these devices have the disadvantage that their soft and flexible properties make them difficult to insert, direct, and place in their correct position inside of the patient's airway. This is due to the fact that, because of their soft and flexible properties, the forces that the doctor exerts on the proximal part of these devices from the outside of the mouth are not transferred to the distal part of the device introduced into the airway, which makes it difficult to direct them and place them in their correct position.

There is therefore no anaesthesia device in the state of the art that can at the same time change from rigid mode to soft and flexible mode, and vice-versa, and which allows both ventilation in laryngeal mask mode and intubation in laryngoscope mode with the same device, without the need to lose valuable time in removing one device and introducing another device to restore oxygenation to the patient.

Finally, there are some existing combined devices where a laryngeal mask is combined with one or more integrated channels, with one of these able to perform the function of oxygen administration while at the same time acting as a guide for an endotracheal tube. There are combined devices of this type existing in the prior art, for example, based upon documents EP 1 938 855 A1, US2003/0192548 A1, US 2001/0012923 A1, U.S. Pat. No. 5,303,697, or US 2004/0020491 A1. However, in all of these cases the channels in the laryngeal mask are totally integrated in an inseparable manner, with no provision being made for their separation.

In GB 2 324 040 A a laryngeal mask is described with just a single hollow, tubular body of sufficient size to allow oxygenation of the patient and for the passage of an endotracheal tube in its interior. In this case the possibility of removing the mask while keeping the endotracheal tube inserted in the patient's larynx is considered. However, since the tubular body is flexible, hollow, and closed along its entire length from the inflatable ring until the proximal part that remains at the outside of the teeth. For this purpose it requires special retention and external pushing pieces and in the end the laryngeal mask is removed completely, including the laryngeal ring.

Combined systems of laryngeal masks and endotracheal tubes are also described in documents such as US 2007/02407(22) A1 and U.S. Pat. No. 5,623,921. However, in the first case there are two flexible tubular bodies that are hollow and closed along their entire length from the trachea until the outside of the teeth. One of these goes towards the trachea and the other towards the oesophagus and the possibility of removing the laryngeal mask, while leaving only the endotracheal tube inserted into the patient's larynx is not considered. In the second case there is such a possibility, by splitting or separating the laryngeal mask's tube into two parts along its entire length. This includes the part that is inserted into the patient's larynx. This could involve difficulties in practice. Also, in both cases removal of the entire laryngeal mask involves the removal of the laryngeal ring also.

Finally, document US 2004/0079(36)4 A1 presents a type of laryngeal mask with an inflatable ring. The mask is rigid and has a rigid tubular body that is hollow and closed along its entire length, from the trachea until the outside of the teeth. This body allows oxygenation to occur and an endotracheal tube can be passed concentrically through the interior of the laryngeal mask's tube. This mask is used to restore oxygenation to patients when intubation with a laryngoscope has not been possible. Since it is rigid, it is used for short periods of time to restore the patient's oxygenation by ventilation, and it is also possible to pass an endotracheal tube through its rigid channel so that later, because of its rigidity, this type of laryngeal mask with inflatable ring can be removed in order to avoid putting pressure on the soft tissues and causing injuries and sores in the patient's airway. However, in this apparatus, because of the fact that the endotracheal tube is concentric with the rigid channel which is closed along its entire length, extraction of said rigid channel is not a simple task. It in fact involves disconnection of the oxygen administered to the patient for a few moments. Special retention and external pushing pieces are also required for this. Also, when it is removed the inflatable ring is also removed although it would be desirable to keep it in place in certain cases. Finally, this device also lacks a means of viewing as well as an integrated anti-condensation system which means that the entire process is performed blind. Since there is no viewing possible during manoeuvring for ventilation or for intubation there are risks involved in terms of failure to place it properly and failure of the ventilation and also a risk of performing an oesophageal intubation, which represents a great risk to the life of the patient.

None of these documents allow the rigid parts of the device to be removed from the patient's larynx in a simple and rapid manoeuvre and vice-versa, leaving only the soft parts inside of the patient's larynx. This would prevent the development of wounds and sores in the soft tissues of the airway while also avoiding the need to interrupt the supply of oxygen to the patient at all times. This manoeuvre can also be performed in the reverse direction, reintroducing the rigid part of the device and sliding it around the flexible part from the outside of the mouth until the interior of the patient's glottis so that it will again have rigid properties according to the clinical needs of the patient. For example, in the case of an emergency reintubation after the patient has regained consciousness after surgery is completed. Furthermore, none of these allow the laryngeal mask's inflatable ring to be left inside of the patient's larynx after this manoeuvre, although this can be highly desirable in certain cases. Finally, none of these have the means available for viewing the interior of the larynx with an integrated anti-condensation system. This would allow interior inspection to serve as a guide for the doctor when directing the tube towards its correct position inside of the larynx.

Therefore, the problem to be resolved by the person skilled in the art is to provide a laryngeal mask that overcomes the problems existing in the prior art and which in particular will allow the two functions of ventilation and intubation to be performed in an interchangeable and reversible manner, without stopping the administration of oxygen to the patient. More specifically, the problem to be resolved for the person skilled in the art is that of providing a laryngeal mask that could be changed from rigid mode to soft and flexible mode and vice-versa, at the will of the operator and in a reversible manner. It must also allow ventilation in laryngeal mask mode and intubation in laryngoscope mode using the same device, without losing valuable time while removing one device and introducing the other device to restore oxygenation to the patient, since during this time the patient would be without an oxygen supply to the lungs.

Another objective of the invention consists of providing a laryngoscope that allows the doctor to inspect the inside of the larynx in a manner such that this would serve as a guide when directing the tube towards its proper position inside the larynx.

One further objective of the invention consists of preventing condensation from being deposited on the lenses that make up said means of inspecting the inside of the larynx in a laryngoscope provided with such means of inspection.

The present inventors have found that these problems can be resolved using a laryngeal mask that has two main components: A first component or rigid tube (10), essentially in the form of a "J" and lengthwise open along its entire length. This lengthwise opening is intended to house a second component or flexible tube (20) of a laryngeal mask inside which terminates at its distal end in an inflatable or gel ring (21). This arrangement allows the doctor to comfortably insert the invention's laryngeal mask assembly into the patient's larynx since the assembly is rigid and can be directed and positioned in its proper location with precision and comfort. Once the assembly with both components has been positioned and given that the two components can be separated, the rigid tube (10) can be easily removed from the larynx, leaving only the laryngeal mask with its flexible tube (20) inside which terminates at its distal end at the inflatable or gel ring (21). Due to its softness and flexibility it can remain in the patient's larynx for a long period of time without causing injuries.

In a preferred embodiment, the invention's laryngeal mask also comprises some optical viewing means (30) intended to transmit the image of the interior of the larynx to the doctor or operator outside. These means typically comprise:

- a system of optical lenses (35) to capture the image with this system located in the distal end (33) of a flexible tube (32) that contains in its interior the means of transport (cables, fibre optics, etc.) needed to transmit the image from the system of optical lenses to the mini-video camera (37);
- a mini video camera (37) also located in the distal end (33) of the flexible tube (32);
- a illumination system (38b) for the entire assembly located in the distal end (33) of said flexible tube (32), as well as a screen or monitor (31) where the images captured by the mini-video camera (37) are displayed.

There is also an optical lens system (36) that operates in conjunction with the viewing means described above in order to capture the image and which are located in the distal end of the channel (26) of the flexible tube (20).

In another embodiment, the system also comprises an integrated system to remove the condensation that may form on the lens system for the optical viewing means during ventilation or intubation procedures.

An additional advantage of the present invention is that the distal end of the rigid tube (10) has, in preferred embodiments, a tongue-shaped tab (11), also rigid, which allows soft tissues such as the tongue to be moved aside during introduction of the device into the patient's airway. It also lifts the patient's epiglottis so that it cannot obstruct the passage of the endotracheal tube towards the glottis and, as the case may be, prevents obstruction of the view of the optical viewing means (30) that capture the image from the optical lens that transmits the interior view of the larynx to the video camera. It also prevents obstruction of the flow of oxygen from the exterior towards the patient's lungs.

Once the mask is in its correct location and therefore viewing of the interior of the larynx is no longer required, it is possible to easily remove the tube that contains the optical lens system (30) and, as the case may be, the optical viewing means and the video camera (37), as well as the rigid tube (10) with its rigid distal tongue-shaped tab (11). This takes place in a manner such that what remains inside of the larynx for ventilation of the patient is the flexible laryngeal mask (20) with its flexible sleeve (23) that surrounds the rigid tongue tab (11) and the inflatable ring (21) but without the rigid tongue-shaped tab lifting the epiglottis, in this way, the invented device also includes the function of the tongue-shaped tab lifting the epiglottis which is removable when the doctor requires. When the rigid tongue-shaped tab is removed a flexible sleeve (23) that is covered by the rigid tongue-shaped tab (11) would remain. It has its same shape and is attached to the flexible laryngeal mask.

Another important advantage of devices that are flexible and at the same time rigid like the Laryngeal Video mask (LVM), and explained as one of the preferred embodiments of the invention, is that if the head of a patient with a rigid model of laryngeal mask is moved during surgery, either by need or due to an unexpected situation, this exterior movement is transmitted to the interior. The laryngeal mask's ring will move and be displaced from its correct location to an incorrect one where the patient cannot be ventilated, it is important for optimal oxygenation that during administration of the anaesthesia the ring is not displaced from its correct position.

This does not occur with the laryngeal video mask in flexible mode because based upon the clinical needs it can be transformed from rigid to flexible and vice-versa and it also has a means of viewing.

BRIEF DESCRIPTIONS OF THE FIGURES

FIG. 1: Side view of the laryngeal mask assembly with the three components joined: Rigid tube (10), flexible tube (20), and viewing means (30). In this view the endotracheal tube (40) is seen housed in its guide channel (25).

Figure 2:
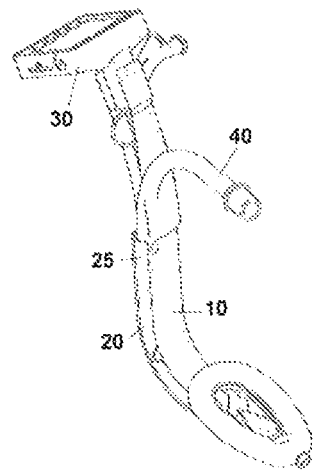

FIG. 2: Perspective view of the laryngeal mask assembly with the three components joined: Rigid tube (10), flexible tube (20), and viewing means (30). In this view the endotracheal tube (40) is seen housed in its guide channel (25).

Figure 3:
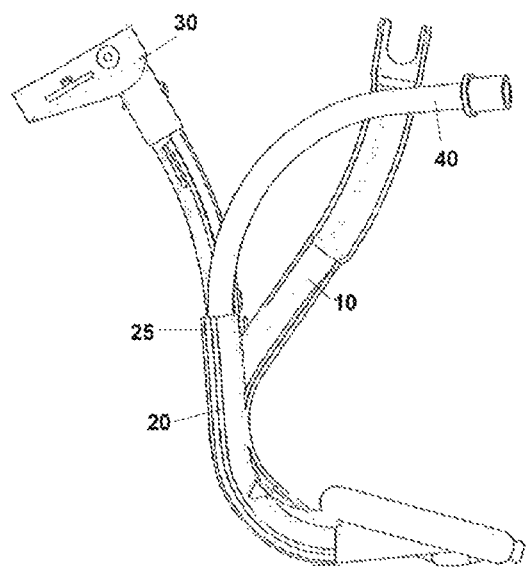

FIG. 3: Side view of the laryngeal mask assembly with the rigid tube (10) halfway through the separation phase from the flexible tube (20), which also has the viewing means (30) housed in one of its channels. In this view the endotracheal tube (40) is seen housed in its guide channel (25).

Figure 4:
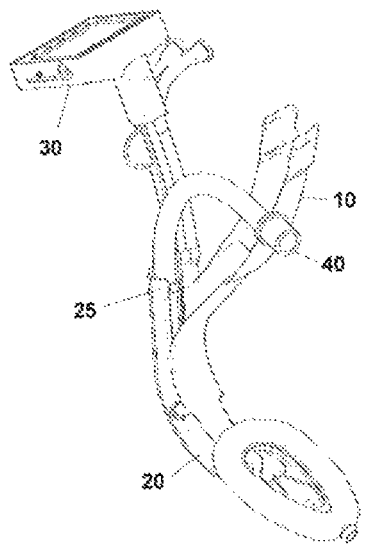

FIG. 4: Perspective view of the laryngeal mask assembly with the rigid tube (10) halfway through the separation phase from the flexible tube (20), which also has the viewing means (30) housed in one of its channels. In this view, the endotracheal tube (40) is seen housed in its guide channel (25).

Figure 5:
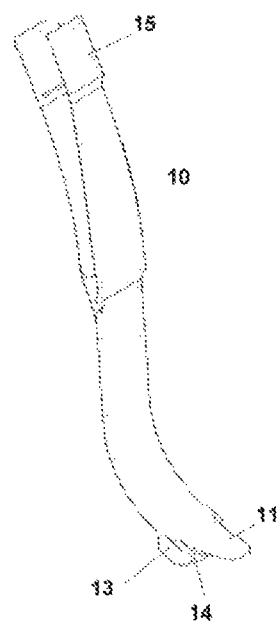

FIG. 5: Perspective view of the rigid tube (10) with the upper rigid tongue-shaped tab (11) and an additional lower rigid tongue-shaped tab (13), where the lower guide rails (14) are going to stop. The proximal assembly area (15) for the viewing means (30) is also seen.

Figure 6:

FIG. 6: Rear view of the rigid tube (10). The lower rigid tongue-shaped tab (13) and the upper rigid rails (12) are seen, as well as the proximal assembly area (15) for the viewing means (30).

Figure 7:
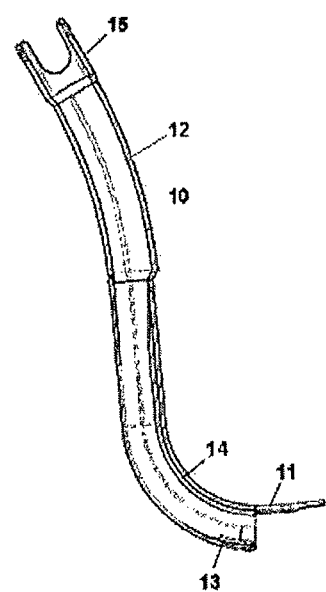

FIG. 7: Side view of the rigid tube (10) with the upper rigid tongue-shaped tab (11) and the lower rigid tongue-shaped tab (13), with the upper guide rails (12) and the lower guide rails (14) also visible. The proximal assembly area (15) for the viewing means (30) is also seen.

Figure 8:
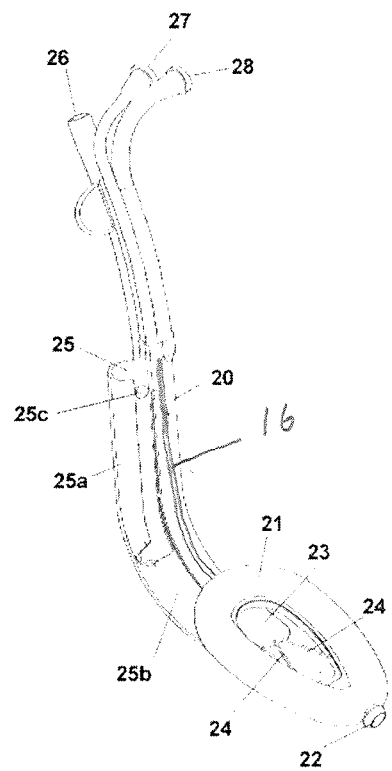

FIG. 8: Perspective view of the flexible tube (20), which has a proximal straight portion, a central curved portion, and a distal inflatable ring or non-inflatable gel ring (21). The four optional channels are seen in the embodiment shown and in the various embodiments any of these may be present independent of the others:

a guide channel (25) for the endotracheal tube (40), which is divided into two sections: one open lengthwise (25a) and the other which is not (25b);

the guide channel (26) for the viewing means (30); this channel (26) has an integrated optical lens that is attached distally to the end of said channel;

the guide channel (27) for aspirating secretions from the distal surface of the integrated optical lens attached distally to the guide channel (26) for the optical means; and the guide channel (28) for the oesophageal aspiration probe, which ends distally in a protuberance (22) that will be the closure area for the oesophageal sphincter.

Also seen within the ring (21) is the flexible sleeve (23), joined by the internal part to the proximal area of the ring (21), which will cover the rigid tongue-shaped tab (11) when the rigid tube (10) is coupled with the flexible tube (20). The flexible sleeve continues distally with two elongations (24) that will be joined distally to the internal area of the ring (21).

Figure 9:
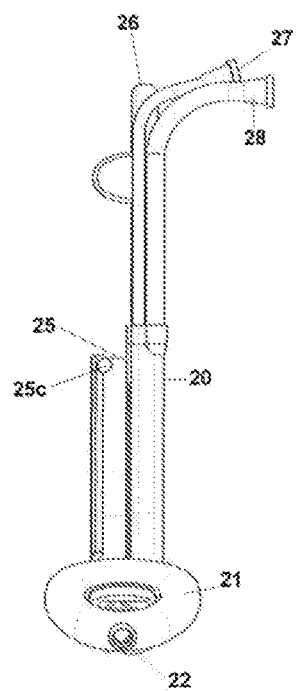

FIG. 9: Front view of the flexible tube (20), which has a proximal straight portion, a central curved portion, and a distal inflatable ring or non-inflatable gel ring (21). Four optional channels present in the embodiment shown are seen, and in the various embodiments any of these may be present independent of the others:

the guide channel (25) for the endotracheal tube (40);

the guide channel (26) for the viewing means (30); this channel (26) has an integrated optical lens that is attached distally to the end of said channel;

the guide channel (27) for aspirating secretions from the distal surface of the integrated optical lens attached distally to the guide channel (26) for the optical means; and the guide channel (28) for the oesophageal aspiration probe, which ends distally in a protuberance (22) that can serve as the closure area for the oesophageal sphincter.

Figure 10:
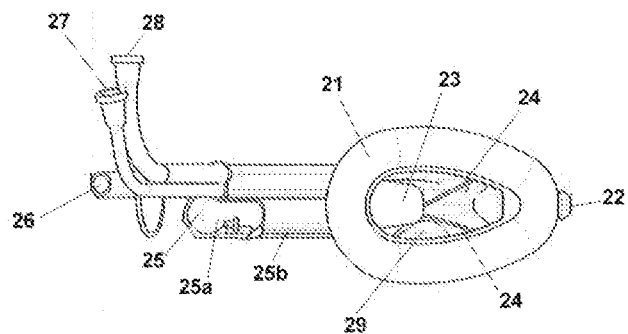

FIG. 10: Upper view of the flexible tube (20), which has a proximal straight portion, a central curving portion, and a distal inflatable ring or non-inflatable gel ring (21). The four optional channels present in this embodiment are seen, and in the various embodiments any of these may be present independent of the others:

a guide channel (25) for the endotracheal tube (40), which is divided into two sections: one open lengthwise (25a) and the other which is not (25b);

the guide channel (26) for the viewing means (30); this channel (26) has an integrated optical lens that is attached distally to the end of said channel;

the guide channel (27) for aspirating secretions from the distal surface of the integrated optical lens attached distally to the guide channel (26) for the optical means; and the guide channel (28) for the oesophageal aspiration probe, which ends distally in a protuberance (22) that can serve as the closure for the oesophageal sphincter.

Also seen within the ring (21) is the flexible sleeve (23), joined by its internal part to the proximal area of the ring (21), which will cover the rigid tongue-shaped tab (11) when the rigid tube (10) is coupled with the flexible tube (20). The flexible sleeve continues distally with two elongations (24) that will be joined distally to the internal area of the ring (21). Also seen within the ring are some "pushers" or projections (29) that will serve to direct the endotracheal tube towards the central axis of the ring (21) and which will also serve to prevent the collapse of the laryngeal mask in the vertical direction.

Figure 11:
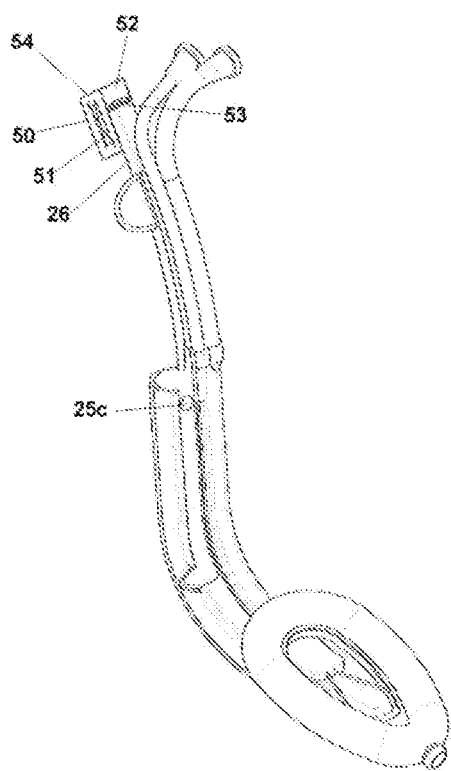

FIG. 11: Perspective view of the flexible tube (20) where the compartment (50) is seen, intended to house the batteries (51) that will supply power for the entire device. This compartment is coupled and joined to the proximal part of the flexible tube (26) by means of a joining area (53). This compartment (50) also has a joining area (52) with the viewing means (30), preferably hollow, and through which the flexible tube (32) for the viewing means (30) passes. This compartment (50) has a joining area (54) with the monitor (31), through which the electricity required by the device will be transmitted.

Figure 12:
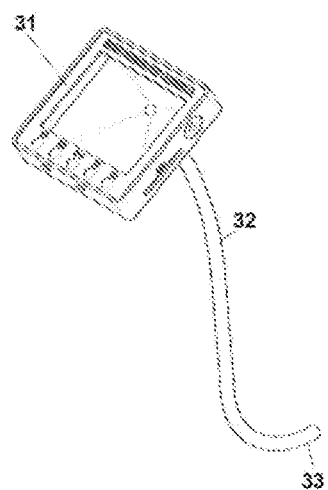

FIG. 12: Perspective view of the viewing means (30), which in the embodiment shown is made up of a monitor (31), a flexible tube (32), and a distal area (33) for housing the camera, the illumination elements, and an optical lens.

Figure 13:
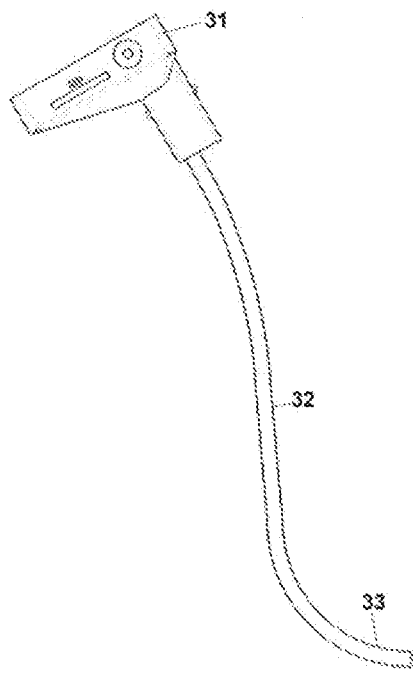

FIG. 13: Side view of the viewing means (30), which in the embodiment shown are made up of a monitor (31), a flexible tube (32) with a distal tubular area (33) for housing the camera, the illumination elements, and an optical lens.

Figure 14:
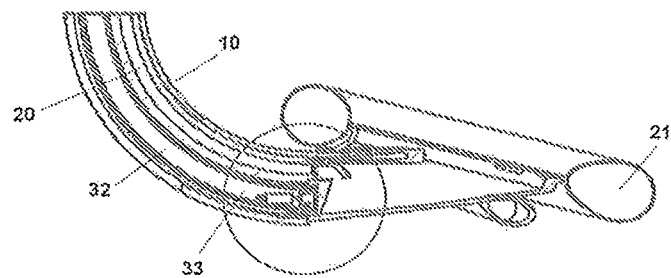

FIG. 14: Transverse section of the end of the assembly of the laryngeal mask, where visible elements include the rigid tube (10), the flexible tube (20), the transmission tube for the viewing means (32), the distal area (33) of the flexible tube (32) where the optical focusing lenses (35) are located, the video camera (37), the illumination means (38b), and the inflatable ring (21).

Figure 15:
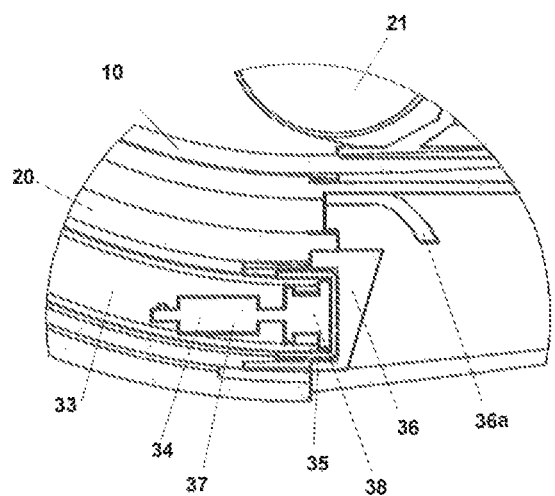

FIG. 15: Expanded portion of FIG. 14, where the elements in FIG. 13 can be seen in more detail: rigid tube (10), flexible tube (20), inflatable ring (21), distal area (33) of the flexible tube (32), video camera (37) comprising its electronics (34) in the proximal area and its optics (38a) in its distal area (38), optical focusing lens (35) that is coupled to the distal area (33) of the flexible tube (32); this optical focusing lens also serves to create the hermetic distal closure (33) for the flexible tube (32); optical focusing lens (36) which is coupled to the distal area of the flexible tube (26); this optical focusing lens (36) also serves to create the hermetic distal closure for the flexible tube (26). The lens (36) has a projection (36a) to direct the aspiration of the flexible tube (27) downward.

Figure 16:
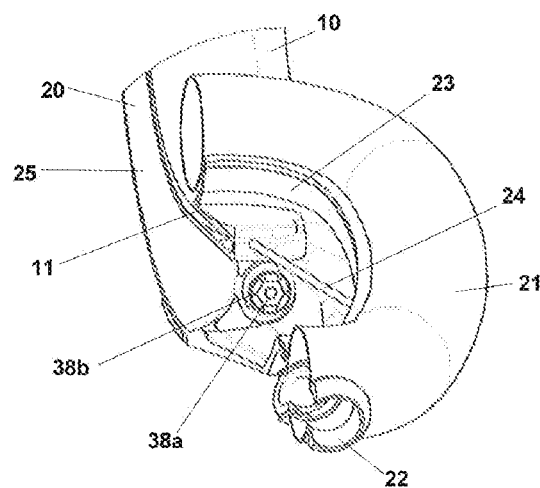

FIG. 16: Expanded portion of FIG. 14 oriented towards the front, where the elements in FIG. 14 can be seen in greater detail: rigid tube (10), flexible tube (20), flexible sleeve (23) that surrounds the rigid tongue-shaped tab (11), elongations (24) of the flexible sleeve (23), inflatable or gel ring (21), distal cover (22) for closure of the oesophageal sphincter, which can be hollow so that an aspiration probe can pass through to the oesophagus, guide channel (25) of the flexible tube (20), optics of the video camera (38a), illumination system (38b).

DETAILED DESCRIPTION OF THE INVENTION

Consequentially, as its primary aspect, the invention is focused on a laryngeal mask comprising the following elements:

a first element which is a hollow rigid tube (10), essentially in the form of a "J", which has a lengthwise opening along its entire length; and a second element which is a flexible tube (20), also essentially in the form of a "J", intended to be housed in the lengthwise opening of the first element (10) and separable from this element. This tube terminates at its distal end with an inflatable or gel larynx ring (21).

In its secondary aspect, the invention is focused on a method for intubation and/or ventilation of a patient using the mask in agreement with any of the previous claims, characterised by comprising the stages of:

a) introducing the laryngeal mask, made up of the first (10) and second (20) elements joined in a manner such that the resulting assembly is substantially rigid, into the patient's larynx, and directing it into the patient's larynx until it is in its correct position; and b) when the doctor considers it to be appropriate, separating the first (10) and the second (20) elements, removing the first rigid element (10) and leaving the second flexible element (20) in the patient's larynx for ventilation.

The laryngeal mask represented by the invention will be described in more detail next, making reference to the attached figures.

The Device's Main Elements:

The laryngeal mask of the invention comprises the following two main elements, specifically:

The first element is a rigid tube (10), essentially in the form of a "J". This rigid form in the shape of a "J" essentially consists of an initial slightly curved proximal section followed by a second straight intermediate section and ending in a third curving distal section. Since it simulates the anatomy of the patient's airway, this shape facilitates the introduction of the laryngeal mask into the airway as well as placement in its correct position there. Because of this shape it is also unnecessary to hyper-extend the patient's neck in order to insert the device. This rigid tube has a lengthwise opening along its entire length, with this opening intended to house the second element, which is essentially a flexible laryngeal mask (20) made up of a flexible tube (26) that terminates at its distal end with an inflatable or gel ring (21). This flexible tube (26) of the second element (20) also is essentially in the shape of a "J". It comprises a straight, flexible proximal section and a curved, flexible distal section that forms a specific angle with the first section, and which has an inflatable or gel ring (21) at the end. This flexible tube (26) serves to guide the flexible tube (32) with the viewing means (30) of the video camera and the optical lens system, in those preferred embodiments of the invention that contain that system.

Optionally, the second element's (20) flexible tube (26) can also have a second tube (25) attached, preferentially made of the same material as the flexible tube, it can be shorter in length and also open lengthwise in its proximal area (25a) and closed in its distal area (25b) in order to serve as a guide channel. This guide channel (25) is intended to house and serve as a guide for the endotracheal tube (40), it preferably has the exact dimensions required in order to house an 8.5 mm endotracheal tube, which is the size most commonly used in adults. Also, in one embodiment this guide channel (25) can optionally be provided on one wall of the proximal area (25a) with a retention system such as the projection (25c), in order to prevent the wall (25a) of the proximal part of the flexible tube (25) from being displaced laterally, and in this way allowing the endotracheal tube (40) that runs through the interior of the channel (25) to be attached. This system can take various forms, one of which can be in the form of a projection or bump (25c), which can run along a groove in the rigid tube (10).

In a preferred embodiment of the invention, the second element (20) is also provided with a system to separate the tissues of the airway and in this way to lift the epiglottis according to the anaesthesia needs of the patient at the moment. This system to separate the tissues of the airway and elevate the epiglottis is made up of a hollow, soft, and flexible sleeve (23), which becomes rigid when the rigid tongue-shaped tab (11) located in the distal end of the first element's rigid tube is inserted into its interior. In certain embodiments, this flexible sleeve (23) is in turn made up of two layers of flexible material that overlap with the proximal part of the interior ring (21) of the laryngeal mask (20), distally towards the centre of said interior ring (21). These two flexible layers can be joined along their entire edge or open at their most distal end in the manner of a Heimlich valve, and they can also be joined with the internal part of the gel ring through the elongations (24).

When the flexible tube (26) of the second element (20) is coupled with the rigid tube (10) of the first element, the distal end (11) of the tongue-shaped tab of the rigid tube (10), which preferentially has a duckbill shape, is inserted inside the two flexible layers of the flexible sleeve (23) of the laryngeal mask (20), from its proximal to distal parts. In this way, the resulting combined tongue-shaped tab changes from having flexible properties to rigid properties. This is useful for separating the airway tissues during the entire length of its travel towards its final correct position. It also serves to prevent these tissues from interfering with the area visible to the optical means as well as to lift the epiglottis. The rigidity of this system helps to actively separate these soft tissues because the movements made to the first rigid element from the outside are transmitted to the interior of the laryngeal mask, to its most distal portion at the rigid tongue-shaped duckbill tab. Then, once the anaesthesia process has advanced and the rigid first element (10) is removed from the assembly, the tongue-shaped tab (11) of the rigid tube (10) is logically also removed from between the two flexible layers of the flexible sleeve (23) of the laryngeal mask (20), with the sleeve (23) in this way regaining its flexible form. In this flexible form, the sleeve (23) can only passively keep the tissues out of the visible area for the optical means, but it cannot serve to actively separate these soft tissues. This is because once the rigid tongue-shaped tab is removed the movements made from the laryngeal mask's exterior are not transmitted as far as the flexible sleeve (23), due to the softness of the material of the flexible tube (26) of the second element (20).

In an optional embodiment, these two flexible layers of the flexible sleeve (23) are joined with the internal area of the ring (21). This takes place through two elongations (24) which extend distally from the distal part of these flexible layers towards the distal part of the ring (21) in the interior of the laryngeal mask (20). These elongations (24) serve to prevent the two flexible layers of the flexible sleeve (23) from falling downwards and impeding the correct vision of the viewing means by interfering with their viewing area. They also serve to passively prevent the soft tissues of the airway and the epiglottis from falling into the bell of the laryngeal mask. These two elongations (24) can also have various arrangements, but the optimal one is a triangular arrangement. This allows more separation distally without causing interference in front of the vision area of the optical means and also allows passage of the endotracheal tube (40) between them.

The second element (20) can also optionally have a projection or stopper (22) in the distal end of the inflatable or gel ring (21), intended to plug the oesophageal sphincter to prevent the exit of oesophageal material into the airway. This is important because there is a great risk caused by materials from the oesophagus being breathed into the lungs and causing pneumonia, which can be fatal in 50% of patients. This projection (22) can be hollow to allow the passage of an aspiration probe into the oesophagus.

In yet another embodiment, the laryngeal mask's bell is provided with at least one "pusher" or projection (29) located inside of it, to prevent the vertical collapse of the laryngeal mask caused by the pressure of the soft tissues in the patient's airway. Thanks to its orientation it can also allow the endotracheal tube (40) to be directed towards the centre of the lengthwise axis of the laryngeal mask device (20), thereby preventing it from heading if in undesired directions and allowing it to enter directly through the centre of the vocal cords.

The Optical Viewing Means and the Anti-Condensation System

To these two main elements (10) and (20), some means for optical viewing are added in preferred embodiments of the invention. These have a variety of functions and advantages: they allow the image to be focused at an appropriate distance from the vocal cords, they allow the axis of vision to be aligned with the axis of movement for the endotracheal tube, and the optical focus lens (35) is located in the distal area (33) of the flexible tube (32) which also makes it possible to hermetically close the distal area (33) of the flexible tube (32). Another optical focus lens (36) is located in the distal area of the flexible tube (26) and allows hermetic closure of the channel (26) of the flexible tube (20), which is where the viewing means (30) of the laryngeal video mask are housed. This keeps them clean and out of contact with the patient's secretions, and prevents the need to resterilise them after each use, allowing them to be used in another case right away.

In a preferred embodiment of the invention the set of optical viewing means is made up by: the optical lens (35) located distally (33) in the flexible tube (32) of the viewing means (30), the integrated optical lens (36) attached distally in the channel (26) of the laryngeal mask (20) that houses the viewing means (30), a video camera (37), a monitor or screen (31) with some menu buttons, a flexible hollow tube (32) through which the wires, fibre optics, or any other means of transmitting the images pass from the lenses to the video camera (37), and the illumination system (38b), with all of these working together plus the anti-condensation system.

The batteries (51) for the device, which provide power for the monitor or screen (31), the video camera system (37), and the illumination system (38b), are located in a compartment (50). This compartment is coupled and joined to the proximal part of the flexible tube (26) by a joining area (53). This compartment (50) also has a joining area (52) with the viewing means (30), which will be hollow and through which the flexible tube (32) for the viewing means (30) will pass. The compartment (50) also has a joining area (54) with the monitor (31) through which the electricity required by the device will be transmitted.

In one embodiment the monitor or screen has some buttons to control the menu as well as an optional recording system, with removable SD memory cards and an optional video output connection.

The assembly of the viewing means can optionally transmit the image to another receiving system by wireless means, for example infrared, Bluetooth, or Wi-Fi.

The set of optical viewing means receives electricity from the batteries (51) that are housed in the compartment (50) and which supply the monitor or screen, the video camera system, and the illumination system. The batteries in the compartment (50) that power the video camera system and the illumination system create sufficient heat to heat the optical lens (35) located distally (33) in the flexible tube (32) with the means for transmitting the images, and this lens (35) heats the integrated optical lens (36), which is distally attached in the channel (26) of the laryngeal mask (20). This prevents condensation caused by the change of temperature that occurs when the device goes from a cold environment to a warm environment with higher humidity, such as the patient's airway. In this configuration the laryngeal mask in the invention can be defined as a laryngeal video mask with optical viewing means and integrated optical lenses.

The viewing system (30) can be attached or detached from the rest of the system by guiding it through the flexible channel (26) of the second element or flexible laryngeal mask (20). Also, as mentioned above, the distal portion of this flexible tube (26) contains the optical lens system (36) which will assist with focusing the video camera (37) and which will also help align the video camera's (37) viewing axis with the sliding and advancement axis of the endotracheal tube (40). It will be heated to form part of the anti-condensation system.

In preferred embodiments of the invention, the anti-condensation system will be located in the distal part (33) of the flexible tube (32), which contains the optical lens system (35). The anti-condensation system integrated into the laryngeal video mask (20) and the illumination system (38b) functions by using contact and proximity to heat the distal optical lens (35) located in the distal end (33) of the flexible tube (32). The optical lens (36) located distally in the channel (26) that guides the flexible tube (32) will also be heated by contact and proximity, increasing its temperature to the temperature of the human body and preventing the production of condensation. This condensation is created by the difference between the colder temperature outside of the patient's body and the warmer and more humid conditions inside the patient's airway.

The System for Aspiration of Oesophageal Secretions

In another preferred embodiment the invention will also include an additional channel (28) that is closed along its entire length but open at both ends, dedicated to aspiration of oesophageal secretions. This channel runs the entire length from the distal part of the inflatable or gel ring (21) of the laryngeal mask (20) to the proximal portion of the laryngeal mask (20), where it can be coupled with a standard surgical aspiration system.

The Aspiration System for Secretions on the Optical System for the Viewing Means In another preferred embodiment, the invention also includes an additional channel (27) closed along its entire length but open at its distal end and optionally closed with a plug on its proximal end. This channel is dedicated to aspiration of secretions on the distal surface of the optical lens (36) located distally in the flexible channel (26) of the laryngeal mask (20). This channel runs the entire distance from the distal part of the flexible channel (26), which guides the flexible tube (32) in its interior, to the height of the distal optical lens (36) in the flexible channel (26), then to the proximal part of the laryngeal mask (20). At that point it can be coupled to a standard surgical aspiration system which will allow cleaning of the optics in the event that the lens becomes obscured by secretions.

The Oxygen Administration Channel

Optionally, the laryngeal mask in the invention can have a channel (25) or conduit for administration of oxygen, closed along its entire length and dedicated or integrated as with the rest of the laryngeal masks on the market or it can also not be closed along its entire length, dedicated or integrated, and in this case with an open channel (25a) or conduit along its entire length except for at the distal end (25b), where a short length will be closed.

In the case where there is not a dedicated or integrated channel or conduit for administration of oxygen but there is a channel or conduit open along its entire length (25a) except for at the distal end (25b), where a short length is closed, an endotracheal tube (40) will be used. This can be any type of standard endotracheal tube manufactured by any endotracheal tube company, where the channel (25b) and the endotracheal tube (40) will perform two functions:

First, to administer oxygen to the patient when this device is used in ventilation mode, where the pneumatic cuff of the endotracheal tube (40) is withdrawn or retracted and strategically located at the height of the distal end of the short closed length of the oxygen administration channel (25b), and when inflated this cuff creates a hermetic closure with the closed channel (25b), allowing ventilation of the patient with positive pressure and without leaks;

The second function will be that of using the channel (25a) or conduit open along its entire length except for a short distance closed at its distal end (25b) to guide the endotracheal tube through the vocal cords, for intubation of the patient when the device is used in intubation mode, in order to perform this intubation manoeuvre the pneumatic cuff of the endotracheal tube (40) must first be deflated in order to advance the endotracheal tube into the closed channel (25b).

An Embodiment of the Invention

In this manner, in agreement with one embodiment of the invention, the flexible part (20) of the device's laryngeal mask has four channels:

a first channel (28) that is completely closed along its entire length but open at its two ends for aspiration of oesophageal secretions, a second channel (27) completely closed along its entire length but open at its distal end, and closed at its proximal end by a cover that can be opened only in cases where there is a need to aspirate secretions from the distal surface of the optical lens (36) of the laryngeal video mask, a third channel (26) completely closed along its entire length but open only in its proximal part, where the viewing means (32) enter, and closed in its distal portion by the optical lens (36) of the laryngeal video mask, and a fourth channel (25) open along almost its entire length (25a) except in its final distal portion, which is closed (25b), and also open at both of its ends, and which will serve as a guide for the standard endotracheal tube (40).

The preferred embodiment of the invention has a rigid part (10) that has a rigid tongue-shaped tab (11) in its distal part.

The preferred embodiment of the invention has dedicated means of optical viewing (30) with an integrated anti-condensation system available.

This preferred embodiment of the invention allows standard endotracheal tubes (40) to be used instead of special silicone endotracheal tubes as is the case in other current state of the art products, and it allows the use of tubes with an internal diameter as large as the 8.5 mm internal diameter that is the most commonly used size in anaesthesia for a normal adult.

In one embodiment of the invention, the sliding between the laryngeal mask's rigid elements (10) and flexible elements (20) for separation or decoupling or later coupling (if necessary) of the two elements will be facilitated by some rails that will run along the entire length of the midline of both the upper part (12) and lower part (14) of the rigid element, as well as by some grooves (16) of the same size located along the midline of the flexible element (20) of the laryngeal mask.

In one embodiment of the invention, the rigid tongue-shaped tab (11) located in the distal part of the first element (10) of the device performs the function of separating the soft tissues of the airway as well as the function of lifting the epiglottis. It also has the function of preventing the horizontal collapse and closure of the laryngeal mask's ring (21), which is produced within the patient's airway when the airway's soft tissues close over the ring (21) of the laryngeal mask (20).

In this embodiment of the invention the mode of administering oxygen to the patient is interchangeable between ventilation mode using the inflatable or gel ring and intubation mode using the endotracheal tube in order to provide more positive pressure to the patient and prevent prolonged pressure in the same area in the soft tissues of the airway, and vice-versa.

Procedure for Ventilation Using the Device in a Preferred Embodiment

Prior to introduction of the device into the patient's airway, the standard endotracheal tube (40) will be withdrawn or retracted into a specific position in the fourth guide channel (25) in the flexible laryngeal mask, so that its pneumatic cuff is positioned precisely in the closed distal part of the guide channel (25b). This cuff will be inflated so that a hermetic closure is made with the closed part of the fourth guide channel (25b), and oxygen for the patient will later be administered through its interior.

The device is then inserted into the patient's airway using the view provided by the optical viewing system (30) with the second flexible element (20) coupled in the lengthwise groove in the first rigid element (10), with the viewing means (30) introduced into the third channel (26) of the flexible mask (20) and with the standard endotracheal tube (40) introduced in the fourth guide channel (25), with its cuff inflated to create a hermetic closure with the closed channel (25b).

Once the device is introduced into the patient's airway until reaching its optimal location using the direct viewing provided by the viewing means (30), the distal inflatable ring of the laryngeal mask is inflated in the case of an inflatable ring model. If the model has a gel ring then the ring would not need to be inflated.

Oxygen is administered by the proximal part of the endotracheal tube (40), and will reach the patient with this device configuration in ventilation mode.

If the patient is receiving controlled and stable oxygenation, then the rigid element (10) can be decoupled and removed by sliding the rails (12) and (14) along their grooves in the laryngeal mask (20), with only the flexible part (20) remaining inside of the patient's airway, and with the endotracheal tube as a connection for transporting oxygen. This prevents pressure on the soft tissues and injuries for the patient.

Here the viewing elements (30) can either be removed or left in their channel (26).

Procedure for Intubation Mode Using the Device in a Preferred Embodiment of the Invention When the doctor requires intubation of the patient with the laryngeal video mask, this begins from the ventilation mode. Once the patient is receiving stable oxygenation in ventilation mode, the pneumatic cuff or ball in the endotracheal tube (40) is deflated, and it is advanced towards the vocal cords until entering the trachea, with continuous viewing during the entire manoeuvre. There the pneumatic cuff or ball in the endotracheal tube (40) is re-inflated against the tissues of the trachea, creating a hermetic closure. Oxygen is then provided to the patient again, now intubated. At this point in time the inflatable ring (21) in the laryngeal mask (20) can be deflated.

Now, when the patient is stable the rigid element (10) can be decoupled and removed by sliding the rails (12) and (14) along their grooves in the laryngeal mask (20), and the deflated flexible mask (20) and the endotracheal tube (40) can be left in for transmitting oxygen to the patient.

The flexible element (20) can also be removed, leaving only the endotracheal tube (40) inside of the patient. To do this, the flexible element (20) is slid towards the outside of the mouth while at the same time a finger is used to maintain the position of the endotracheal tube (40) in the mouth and to prevent it from coming out. Since the channel (25a) is open, the doctor's finger can be used to maintain the position of the tube (40) until the ring (21) has come out of the mouth and the tube (40) can be grasped at the other end of the ring (21). The closed channel (25b) is short in length and its dimensions coincide exactly to allow this extraction manoeuvre to be performed for the flexible mask (20), leaving only the tube (40) in the patient's airway. The tube is first held in place by the channel side (25b) and then held in place by the ring side (21).

The invention claimed is:

1. A laryngeal mask comprising the following elements:
   a rigid tube essentially in the form of a "J", which has a lengthwise opening along its entire length; and
   a flexible tube, also essentially in the form of a "J", configured to be housed in the lengthwise opening of the rigid tube and separable from the rigid tube, and terminating at its distal end with an inflatable or gel laryngeal ring;
   wherein the rigid tube terminates at its distal end with a rigid tongue-shaped tab, and wherein the flexible tube terminates at its distal end with a flexible sleeve configured to house the rigid tongue-shaped tab of the rigid tube in the interior of the flexible sleeve when the rigid tube and the flexible tube are coupled.

2. The laryngeal mask according to claim 1, wherein the flexible tube also has a first guide channel attached, configured to house an endotracheal tube inside thereof.

3. The laryngeal mask according to claim 2, wherein the flexible tube has a second guide channel attached to house a flexible tube of viewing means.

4. The laryngeal mask according to claim 3, wherein the flexible tube also has a third guide channel attached for aspiration of secretions from the distal surface of an optical lens.

5. The laryngeal mask according to claim 4, wherein the flexible tube also has a fourth guide channel attached, is configured to house an oesophagal aspiration probe.

6. The surgical mask according to claim 5, wherein the fourth guide channel terminates distally in a protuberance or plug configured to close an oesophagal sphincter.

7. The laryngeal mask according to claim 6, wherein the protuberance or plug is provided with an orifice that is configured for the oesophagal aspiration probe to pass through it.

8. The laryngeal mask according to claim 3, wherein the second guide channel is provided with an optical lens at its distal end, which is integrated and moves together with the second guide channel.

9. The laryngeal mask according to claim 3, wherein the second guide channel is provided with a compartment at its proximal end, which contains some batteries configured to supply electricity to components of the mask that require it.

10. The laryngeal mask according to claim 2, which contains viewing means for capturing images from the interior of a patient's larynx and display them on the exterior.

11. The laryngeal mask according to claim 10, wherein the viewing means comprise: a second flexible tube configured to be housed in the interior of a second guide channel, and which contains means for transmission of images, and wherein said second flexible tube is provided with an optical focusing lens at its distal end, a video camera, and provided at its proximal end with a monitor for displaying the images captured by the video camera.

12. The laryngeal mask according to claim 11, in which the means contained in the flexible tube-for transmitting the images are copper wires or fibre optic.

13. The laryngeal mask according to claim 11, in which the monitor is autonomous and independent of the mask and where the viewing means comprise means to send the images captured by the video camera to a monitor in a wireless manner.

14. The laryngeal mask according to claim 11, in which the viewing means also include an anti-condensation system comprising a heating/illumination system for heating an optical lens located at the distal end of the second flexible tube, as well as for heating the optical lens located at the distal end of the second guide channel.

15. The laryngeal mask according to claim 2, wherein the first guide channel houses an endotracheal tube in its interior and is divided into one area that is lengthwise open and another area that is not open.

16. The laryngeal mask according to claim 15, wherein the guide channel is also provided, in a wall of the open area, with a projection, which is fittable into a groove in the rigid tube, to prevent the wall from becoming laterally displaced, allowing the endotracheal tube that runs through the inside of the channel to be held in place.

17. The laryngeal mask according to claim 2, wherein the dimensions of the first guide channel houses an endotracheal tube that has an 8.5 mm internal diameter in the interior thereof.

18. The laryngeal mask according to claim 1, wherein the flexible sleeve is composed of two flexible layers joined along their entire outline.

19. The laryngeal mask according to claim 1, wherein the flexible sleeve is joined by its distal end to the internal face of the laryngeal ring by means of two elongations.

20. The laryngeal mask according to claim 1, wherein the internal face of the laryngeal ring is further provided with at least one projection configured to direct an endotracheal tube towards the central axis of the ring.

21. The mask according to claim 1, in which the rigid tube is provided with rails that run along at least part of its length, and where the flexible tube is provided with grooves that also run along at least part of its length, the rails and grooves are configured to facilitate coupling and uncoupling of the rigid and flexible tubes.

* * * * *